US011229544B2

(12) United States Patent
Halsne et al.

(10) Patent No.: US 11,229,544 B2
(45) Date of Patent: Jan. 25, 2022

(54) PARASTOMAL HERNIA SUPPORT HARNESS

(71) Applicant: University of Washington, Seattle, WA (US)

(72) Inventors: Elizabeth Halsne, Seattle, WA (US); Mika N. Sinanan, Seattle, WA (US); Kasey Acob, Seattle, WA (US); Wasinee Opal Sriapha, Seattle, WA (US); Nicole Chin, Seattle, WA (US)

(73) Assignee: University of Washington, Seattle, WA (US)

( * ) Notice: Subject to any disclaimer, the term of this patent is extended or adjusted under 35 U.S.C. 154(b) by 830 days.

(21) Appl. No.: 15/909,868

(22) Filed: Mar. 1, 2018

(65) Prior Publication Data

US 2018/0250158 A1 Sep. 6, 2018

Related U.S. Application Data

(60) Provisional application No. 62/465,281, filed on Mar. 1, 2017.

(51) Int. Cl.
*A61F 5/449* (2006.01)
*A61F 5/44* (2006.01)
*A61F 5/445* (2006.01)
*A61F 5/443* (2006.01)

(52) U.S. Cl.
CPC .......... *A61F 5/449* (2013.01); *A61F 5/4404* (2013.01); *A61F 5/443* (2013.01)

(58) Field of Classification Search
CPC combination set(s) only.
See application file for complete search history.

(56) References Cited

U.S. PATENT DOCUMENTS 1,922,763 A * 8/1933 Gricks .................... A61F 5/445
                                                            604/340
2,063,382 A * 12/1936 Homan .................... A61F 5/34
                                                            128/117.1

(Continued)

FOREIGN PATENT DOCUMENTS

CN          203598093 U          5/2014

OTHER PUBLICATIONS

Aquina, C.T. et al., "Parastomal Hernia: A Growing Problem with New Solutions," Digestive Surgery, Dec. 13, 2014; 31:366-376.

(Continued)

*Primary Examiner* — Guy K Townsend
(74) *Attorney, Agent, or Firm* — Perkins Coie LLP (57) ABSTRACT

Parastomal hernia support devices are disclosed herein. A parastomal hernia support device configured in accordance with embodiments of the present technology can include, for example, a support assembly including a generally rigid outer portion and a generally flexible inner portion having an aperture configured to be aligned with a stoma of the user. In some embodiments, the support assembly includes a tensioning assembly that can be actuated by the user to adjust the tension in a non-elastic strap that secures the support assembly against the user. For example, the user can increase the tension in the strap to add support to the peristomal tissues proximate the stoma to reduce the likelihood of the user developing a parastomal hernia.

15 Claims, 4 Drawing Sheets

(56) References Cited

U.S. PATENT DOCUMENTS

| | | | | | |
|---|---|---|---|---|---|
| 2,127,834 | A | * | 8/1938 | Spindell | A61F 5/449 604/345 |
| 2,496,175 | A | * | 1/1950 | Perry | A61F 5/445 604/335 |
| 2,549,649 | A | * | 4/1951 | Van Hove | A61F 5/445 604/341 |
| 2,656,838 | A | * | 10/1953 | McConnell | A61F 5/445 604/340 |
| 2,675,001 | A | * | 4/1954 | Jones | A61F 5/445 604/343 |
| 2,675,002 | A | * | 4/1954 | Cesare | A61F 5/445 604/338 |
| 2,895,476 | A | * | 7/1959 | Hallard | A61F 5/449 604/400 |
| 3,006,343 | A | * | 10/1961 | Baxter | A61F 5/445 604/343 |
| 3,074,404 | A | * | 1/1963 | Robinson | A61F 5/448 604/338 |
| 3,076,458 | A | * | 2/1963 | Mason | A61F 5/448 604/339 |
| 3,283,757 | A | * | 11/1966 | Nelson | A61F 5/448 604/334 |
| 3,398,744 | A | * | 8/1968 | Hooper | A61F 5/445 604/340 |
| 3,773,048 | A | * | 11/1973 | Kirkliauskas | A61F 5/445 604/345 |
| 4,596,566 | A | * | 6/1986 | Kay | A61F 5/445 604/176 |
| 4,723,952 | A | * | 2/1988 | Esposito | A61F 5/448 604/338 |
| 5,178,614 | A | * | 1/1993 | McDowell | A61F 5/445 604/332 |
| 5,209,744 | A | * | 5/1993 | Abe | A61F 5/445 604/332 |
| 5,338,315 | A | * | 8/1994 | Baker | A61F 5/445 128/888 |
| 5,626,570 | A | * | 5/1997 | Gallo | A61F 5/449 2/49.2 |
| 6,112,704 | A | * | 9/2000 | Altafi | A61F 5/24 128/96.1 |
| 6,328,721 | B1 | * | 12/2001 | Prohaska | A61F 5/449 604/338 |
| 7,540,861 | B1 | * | 6/2009 | Voto | A61F 5/443 604/343 |
| 7,935,097 | B1 | * | 5/2011 | Moore | A61F 5/449 604/345 |
| 10,070,987 | B2 | * | 9/2018 | Scott | A61F 5/4404 |
| 2005/0256466 | A1 | * | 11/2005 | Winkler | A61F 5/449 604/337 |
| 2013/0035654 | A1 | * | 2/2013 | Friske | A61F 5/449 604/344 |
| 2014/0276500 | A1 | * | 9/2014 | Scott | A61F 5/4404 604/343 |
| 2015/0059206 | A1 | * | 3/2015 | Lovett | F16G 11/02 36/50.1 |
| 2016/0058130 | A1 | * | 3/2016 | Boney | A61G 1/044 24/712.6 |
| 2019/0015243 | A1 | * | 1/2019 | Scott | A61F 5/449 |

OTHER PUBLICATIONS

Arumugam, L. et al., "A prospective audit of stomas-analysis of risk factors and complications and their management," Colorectal Disease, 2003 5, pp. 49-52.

Boyles, A., "Stoma and peristomal complications: Predisposing factors and management," Clinical Stoma Care, vol. 8, No. 7, Sep. 2010, pp. 26-36.

Butler, D.L., "Early Postoperative Complications Following Ostomy Surgery," Ostomy Care, 2009; 36(5): 513-519.

Carne, P.W.G. et al., "Parastomal hernia," British Journal of Surgery 2003; 90, pp. 784-793.

Chang, D.T.S. et al., "First Report of the Stapled Mesh Stoma Reinforcement Technique in a Urologic Context," Hindawi, vol. 2014, 3 pages.

"Ostomy Belt with Peristomal Hernia Support," Heatlhcare Common Procedure Coding System, 2019, 6 pages.

Hotouras, A. et al., "Parastomal Hernia Prevention: Is It All About Mesh Reinforcement?" Letters to the Editor, Diseases of the Colon and Rectum, vol. 57: 12 (2014), 2 pages.

Thompson, M.J., "Parastomal hernia: incidence, prevention and treatment strategies," British Journal of Nursing, 2008, vol. 17, No. 2, 5 pages.

* cited by examiner

PARASTOMAL HERNIA SUPPORT HARNESS

CROSS-REFERENCE TO RELATED APPLICATION

The present application claims priority to U.S. Provisional Application No. 62/465,281, filed Mar. 1, 2017, and titled PARASTOMAL HERNIA SUPPORT HARNESS, which is incorporated herein by reference in its entirety.

TECHNICAL FIELD

The present technology relates generally to medical devices for reducing the risk of an individual developing a parastomal hernia. In particular, some embodiments of the present technology are directed to a wearable device for applying pressure proximate to a stoma of an individual wearing the device.

BACKGROUND

An intestinal stoma is a surgically-created opening in the abdomen through which a portion of the intestine is brought to allow waste to exit from the intestines into, for example, a bag. Stoma formation surgery (e.g., a colostomy) is the surgical procedure in which the stoma is formed by drawing a portion of the intestine (e.g., a healthy portion) through an incision in the abdominal wall and suturing it into place. Patients require the formation of stomas as a result of many intestinal disorders, including inflammatory bowel disease and cancer (e.g., colon, rectal, or bladder). As of 2016, 1.2 million Americans are living with stomas, and this population is growing by 3% every year.

For patients who have undergone stoma formation surgery, enlargement of the abdominal wall opening through which the bowel exits (i.e., a "parastomal" hernia) is a common and potentially risky development, occurring in up to 78% of individuals having undergone a colostomy. Parastomal hernias develop due to weakness in the abdominal wall that is a result of disrupting the normal muscular support layers of the abdomen, then made worse by activities that increase abdominal strain (e.g., sneezing, bending over, picking up heavy objects, etc.). Other risk factors for developing a parastomal hernia include loop stomas (small and large bowel), obesity, malnutrition, and other metabolic/physiological conditions predisposing a patient to poor wound healing or increased intraabdominal pressure.

Parastomal hernias put the bowel at risk for twisting and obstruction and make management of the stoma more difficult due to increased leakage and skin ulceration under external stoma appliances. Surgical repair—including moving the stoma to another location in the abdomen and repairing the hernia site and/or implanting a reinforcing prosthetic mesh internally on the abdominal wall around the stoma—are costly, complex, and even with repair, there is a high recurrence rate. Furthermore, surgical repair is often not a safe option for medically-fragile patients. Prophylactic measures to reduce the likelihood of parastomal hernia development at the time of an initial surgical procedure add some risk and complexity and duration to what are already long anesthesia cases. Accordingly, there is a need in the art for improved methods of treating and preventing parastomal herniation.

BRIEF DESCRIPTION OF THE DRAWINGS

Many aspects of the present disclosure can be better understood with reference to the following drawings. The components in the drawings are not necessarily to scale. Instead, emphasis is placed on clearly illustrating the principles of the present disclosure.

DETAILED DESCRIPTION

Aspects of the present disclosure are directed generally toward wearable devices for treating parastomal hernias and/or reducing the likelihood of a wearer developing a parastomal hernia. In several of the embodiments described below, a wearable device includes a support assembly secured against the abdomen of a wearer by a strap and configured to provide supportive force to the abdomen of the wearer. The support assembly includes a generally rigid support panel and a lining coupled to a rear side of the support panel. The lining can be formed from a generally soft and/or flexible material and includes an aperture that can be aligned with the stoma to localize support forces proximate to—but not on—the stoma when the device is worn. The device can further include a tensioning assembly coupled to the support panel and movable by the wearer to adjust the tension in the strap. When tightened against the wearer, the support assembly can apply continuous pressure around the site of the stoma to reduce the likelihood of the wearer developing a parastomal hernia by, for example, flattening the abdominal wall and helping keep the herniated bowel "reduced"—that is, within the abdomen—rather than out of the abdomen within the abdominal wall.

Current noninvasive solutions for treating parastomal hernias or reducing the likelihood of their development include elastic hernia belts. Such conventional hernia belts are often complex to adjust and difficult to don and doff without assistance. Moreover, such conventional belts can shift and become displaced significantly during activity, and can therefore be uncomfortable to wear and provide poor mechanical support around a stoma. In particular, movement or displacement of the belt can cause a stoma appliance in fluid communication with the stoma to leak, which can cause skin irritation and general discomfort for the wearer. These limitations often lead patients to discontinue using such conventional hernia belts—even against the instructions of a treating physician—thereby increasing their chances of developing a parastomal hernia.

In contrast with conventional devices, a parastomal hernia support device configured in accordance with embodiments of the present technology is expected to provide effective abdominal wall support against parastomal herniation without moving significantly during activity of the wearer, and can be simple to don, doff, and adjust. Accordingly, devices configured in accordance with the present technology are expected to improve patient comfort and encourage patient compliance to use the device regularly, thus reducing the incidence or worsening of parastomal herniation.

Specific details of several embodiments of the present technology are described herein with reference to FIGS. 1-5. However, the present technology may be practiced without some of these specific details. In some instances, well-known structures and techniques have not been shown in detail so as not to obscure the present technology. The terminology used in the description presented below is intended to be interpreted in its broadest reasonable manner, even though it is being used in conjunction with a detailed description of certain specific embodiments of the disclosure. Certain terms may even be emphasized below; however, any terminology intended to be interpreted in any restricted manner will be overtly and specifically defined as such in this Detailed Description section.

The accompanying Figures depict embodiments of the present technology and are not intended to be limiting of its scope. The sizes of various depicted elements are not necessarily drawn to scale, and these various elements may be arbitrarily enlarged to improve legibility. Component details may be abstracted in the Figures to exclude details such as position of components and certain precise connections between such components when such details are unnecessary for a complete understanding of how to make and use the present technology. Many of the details, dimensions, angles, and other features shown in the Figures are merely illustrative of particular embodiments of the disclosure. Accordingly, other embodiments can have other details, dimensions, angles, and features without departing from the spirit or scope of the present technology.

Figure 1:
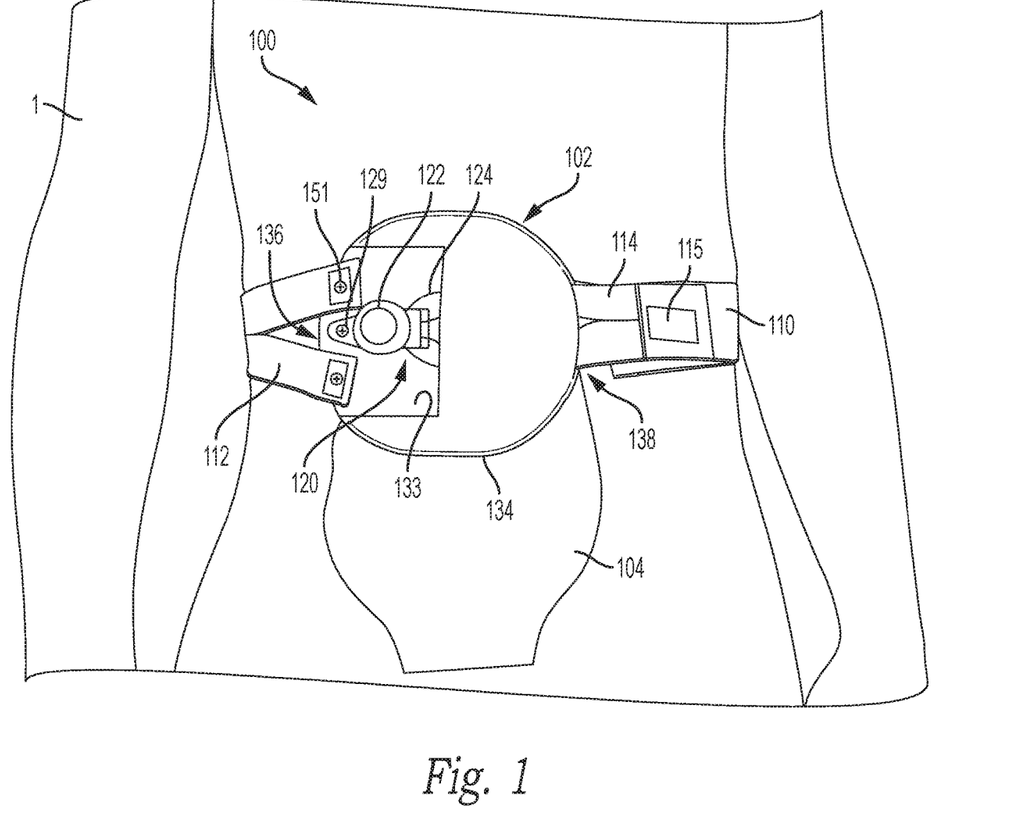
FIG. 1 is a front view of a wearable device secured against the abdomen of a human wearer for reducing the risk of the wearer developing a parastomal hernia in accordance with embodiments of the present technology.

FIG. 1 is a front view of a wearable parastomal hernia support device 100 ("device 100"; a parastomal hernia support harness) configured in accordance with embodiments of the present technology. The device 100 is expected to reduce the risk of a human patient 1 (e.g., a user, a wearer, etc.) developing a parastomal hernia. In some embodiments, the device 100 can additionally or alternatively inhibit the worsening of an existing parastomal hernia of the patient 1. The device 100 includes a support assembly 102, a non-elastic strap 110 coupled to the support assembly 102, and a tensioning assembly 120 coupled to the strap 110 and a front side of the support assembly 102 that faces away from the patient 1 when the device 100 is worn. In the illustrated embodiment, the strap 110 extends around the torso of the patient 1 to secure the support assembly 102 against the abdomen of the patient 1 over and around a stoma (obscured in FIG. 1) in the abdomen of the patient 1. In some embodiments, the support assembly 102 is positioned over a stoma appliance 104 (e.g., including a wafer, flange, and/or bag) that is in fluid communication with the stoma for receiving fecal matter or other waste. The tensioning assembly 120 is configured to adjust the tension in the strap 110 to, for example, increase or decrease a force applied by the support assembly 102 proximate to the stoma of the patient 1.

Figure 2:
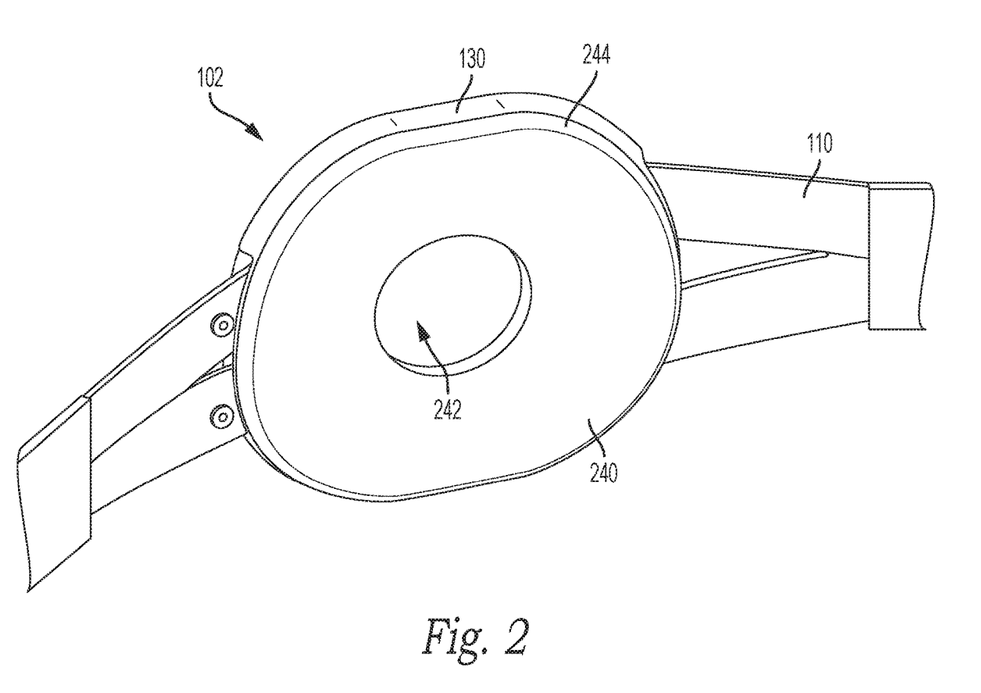
FIGS. 2 and 3 are rear and front isometric views, respectively, of the wearable device shown in FIG. 1.
Figure 3:
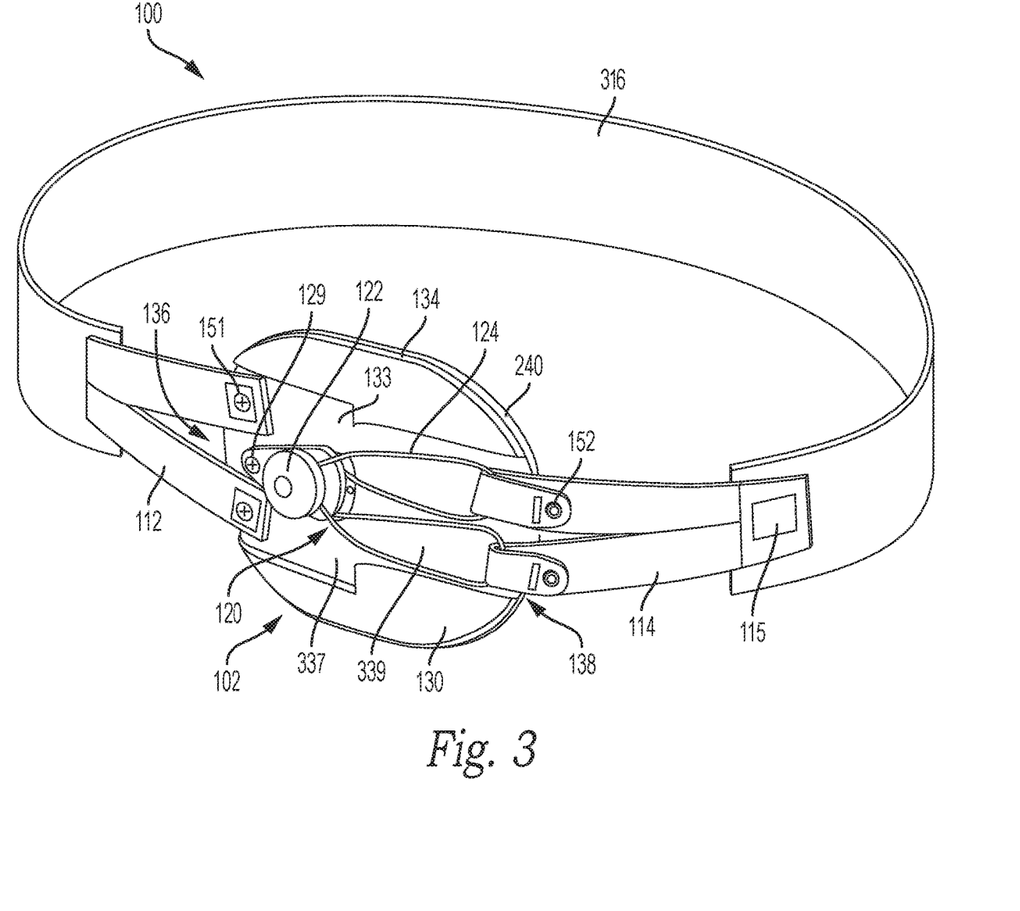

FIG. 2 is a rear isometric view of the device 100 shown in FIG. 1 (before being worn by the patient 1), and FIG. 3 is a front isometric view of the device 100 (also removed from the patient 1) with a portion of the support assembly 102 removed for the sake of clarity. Referring first to FIGS. 1 and 2 together, the support assembly 102 can include a support plate or support panel 130, and an interface or lining 240 coupled to a rear side of the support panel 130 that faces the patient 1 when the device 100 is worn. In some embodiments, the support panel 130 is formed from a material that is more rigid (e.g., firm, inflexible, hard, etc.) than a material used to form the lining 240. For example, the support panel 130 can be formed from a thermoplastic while the lining 240 is formed from a foam. When the device 100 is worn, the rigid support panel 130 transmits pressure onto the abdomen of the patient 1 around the stoma via the softer lining 240. In other embodiments, the support assembly 102 can be an integral member having, for example, a generally rigid outer portion defining an outer surface and a generally flexible inner portion defining an inner surface that faces the patient 1 when the device 100 is worn.

In the illustrated embodiment, the support panel 130 has a generally concave and oval shape that can, for example, conform to the abdominal curvature of the patient 1. In some embodiments, the support panel 130 can be customized to have a curvature and/or size that fits the specific abdominal dimensions of the patient 1 proximate the stoma site. In certain embodiments, for example, the support panel 130 can be custom-formed using a suitable 3-dimensional ("3D") printing process (e.g., 3D printed using any type of 1.75 mm PLA filament or stereolithography method) based on the measured dimensions of the abdomen of the patient 1. The oval shape of the support panel 130 can provide sustained support to the abdominal wall around the stoma, even during changes in abdominal contour resulting from patient activity or postural adjustments. In some embodiments, the oval shape helps reduce rotational displacement commonly associated with square or triangular straight-line edges which may contact a belt or pant line of the patient 1. In other embodiments, however, the support panel 130 can have other shapes such as, for example, circular, rectangular, square, rectilinear, polygonal, oblong, irregular, etc.

In the illustrated embodiment, the lining 240 is coupled to substantially the entire rear side of the support panel 130 and can therefore have a corresponding generally concave oval shape. In some embodiments, for example, the lining 240 can be cut to fit the support panel 130 and then adhered to the rear side of the support panel 130 using an adhesive (e.g., a biocompatible adhesive). In other embodiments, the lining 240 can be coupled to only a portion of the rear side of the support panel 130, can have a different shape than the support panel 130, and/or can be coupled to the support panel 130 via fasteners (e.g., screws, clips, etc.) or other suitable components. The lining 240 includes an aperture 242 formed therein and configured to be aligned with and positioned over the stoma of the patient 1. Therefore, during use, the device 100 localizes the support forces provided by the device 100 around the stoma without pressing on the sensitive intestinal tissues that comprise the stoma itself. In the illustrated embodiment, the aperture 242 has a generally circular shape while, in other embodiments, the aperture 242 can have other shapes such as, for example, circular, rectangular, square, rectilinear, polygonal, oblong, irregular, etc. In some embodiments, the aperture 242 can be custom-formed to have a diameter that is approximately the same size or slightly greater than a diameter of the stoma of the patient 1. In certain embodiments, for example, the aperture 242 can have a minimum diameter of about 2.0 inches and a maximum diameter that is determined by patient compatibility. In some embodiments, the support panel 130 can include an aperture or opening that is generally aligned with the aperture 242 of the lining 240 to expose the stoma site and allow the patient 1 to choose whether they want to (a) draw the stoma appliance 104 through the aperture 242 and the aperture in the support panel 130 or (b) position the stoma appliance 104 flush against their abdomen to exit underneath the support panel 130.

In some embodiments, the lining 240 is formed from a biocompatible foam that can be easy to clean and maintain. For example, the lining 240 can comprise a medical-grade, closed-cell foam such as a high-density polyvinyl alcohol (PVA) foam. In certain embodiments, the lining 240 can have a constant hardness (e.g., a constant Shore 30A durometer), thickness (e.g., about 0.5 inch), and/or density. In other embodiments, the lining 240 can have a variable hardness, thickness, and/or density for variably distributing the support forces provided by the device 100. For example, the lining 240 can have a variable hardness, density, and/or thickness that decreases in a direction radially away from the aperture 242. That is, the lining 240 can have a first hardness/thickness/density proximate to an outer edge 244 of the lining 240 that is less than a second hardness/thickness/density proximate to the aperture 242. Accordingly, in such embodiments, the lining 240 can transmit (a) a greater force adjacent to the stoma where there is a corresponding greater risk of herniation, and (b) a lesser force farther from the stoma to avoid potentially uncomfortable pressure where the risk of herniation is smaller.

Figure 4:
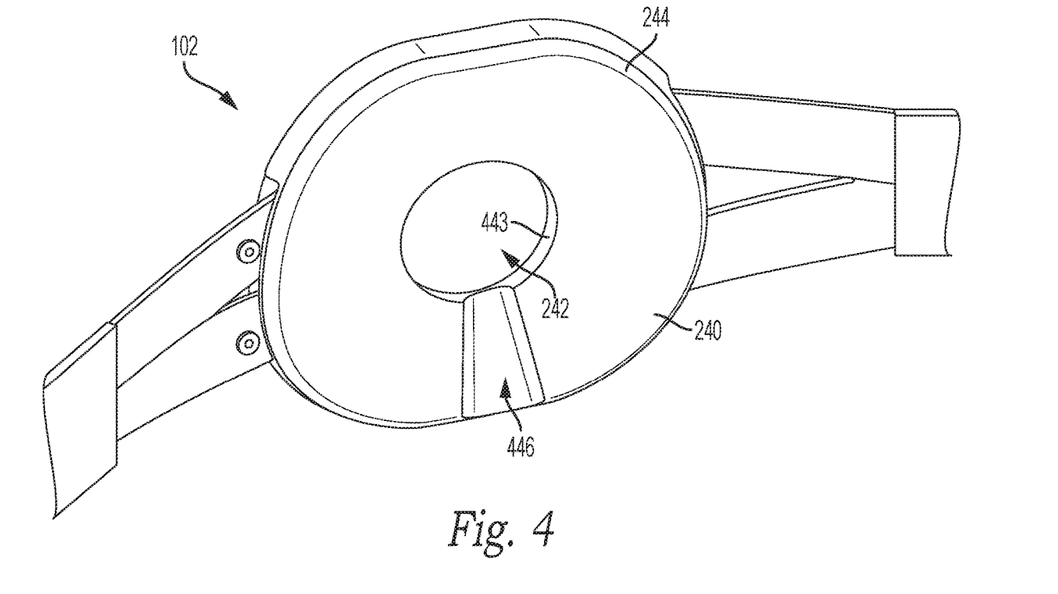
FIGS. 4 and 5 are rear isometric views of the wearable device shown in FIG. 1 having non-planar features for facilitating the drainage of stoma contents in accordance with embodiments of the present technology.

In some embodiments, the lining 240 can include at-least one non-planar feature configured to facilitate drainage of stoma contents into the stoma appliance 104 without compromising the support forces provided by the lining 240. For example, FIG. 4 is a rear isometric view of the device 100 and including a channel 446 extending at least partially into the lining 240. In the illustrated embodiment, the channel 446 extends generally downward from the aperture 242 to the outer edge 244 of the lining 240. Moreover, the channel 446 has a tapered shape having a cross-sectional dimension (e.g., diameter) that increases in a direction radially away from the aperture 242. In other embodiments, the channel 446 can have other shapes and configurations, can extend in different directions along the lining 240 (e.g., laterally), and/or can extend entirely through the lining 240. The channel 446 permits stoma contents to drain downward into the stoma appliance 104 (e.g., into an ostomy bag positioned flush against the abdomen of the patient 1). For example, the channel 446 can allow fluids and gases inside of the stoma appliance 104 to move more easily through and within the stoma appliance 104. Thus, in some embodiments, the channel 446 can inhibit or entirely prevent uncomfortable noises and/or leaks resulting from changes in pressure in the stoma appliance 104 during activity or postural changes by the patient 1. Moreover, because the channel 446 is contiguous with only a relatively small portion of a perimeter (e.g., an edge, a circumference, etc.) 443 of the aperture 242, the channel 446 does not significantly reduce or comprise the support forces transmitted by the lining 240 proximate to the stoma.

Figure 5:
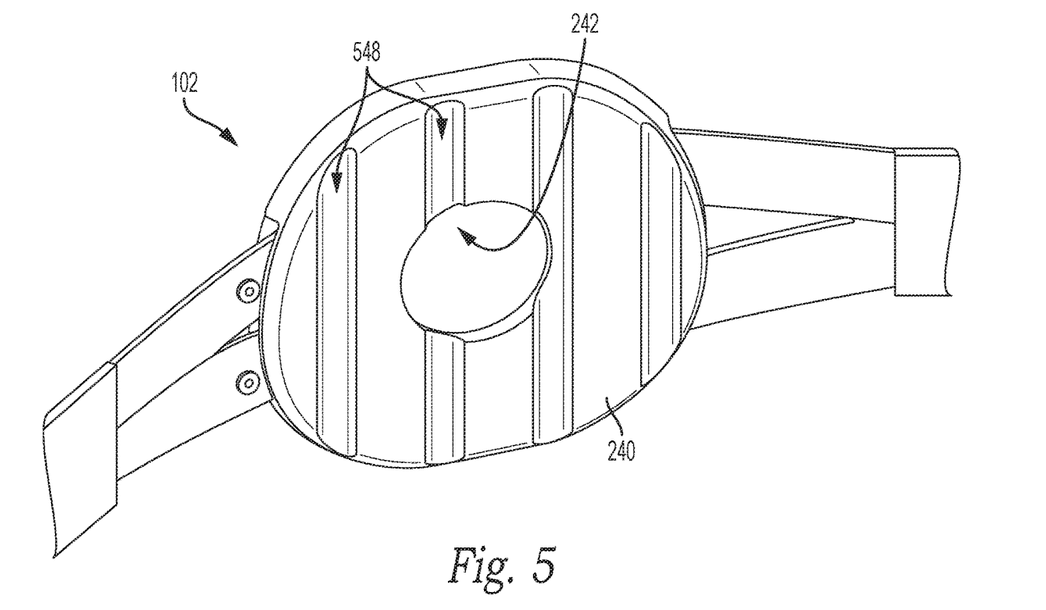

Similarly, FIG. 5 is a rear isometric view of the device 100 and including a plurality of grooves 548 extending at least partially into the lining 240. In the illustrated embodiment, the grooves 548 extend generally vertically across the lining 240 and are arranged generally parallel one another. In other embodiments, the device 100 can include more or fewer than the four illustrated grooves 548, and the grooves 548 can have other shapes or configurations (e.g., angled relative to one another, extending only partially across the lining 240, having a varying depth, etc.). The grooves 548 permit stoma contents to drain into and move through the stoma appliance 104 without comprising the support forces provided by the device 100. In general, the lining 240 can include any suitable non-planar feature (e.g., grooves, channels, ridges, etc.) such that the lining 240 does not completely seal the stoma appliance 104 (e.g., block the movement of stoma contents).

Referring next to FIGS. 1 and 3 together, in some embodiments, a portion of the tensioning assembly 120 can be at least partially concealed within the support panel 130. In the illustrated embodiment, for example, the support panel 130 includes an outer edge 134 having a first edge portion 136, a second edge portion 138 generally opposite the first edge portion 136, and a channel 133 extending along the front side of the support panel 130 generally between the first and second edge portions 136, 138. A first portion of the channel 133 can be exposed at the front side of the support panel 130 to define a recessed portion 337 of the support panel 130, while a second portion of the channel 133 can be covered (e.g., enclosed) to define a tunnel portion 339 of the support panel 130. In the illustrated embodiment, the channel 133 has a varying cross-sectional dimension (e.g., a vertical width) such that the recessed portion 337 and the tunnel portion 339 have different vertical widths. In certain embodiments, for example, the recessed portion 337 has a vertical width of about 3.4 inches and the tunnel portion 339 has a vertical width of about 2.0 inches or greater. In other embodiments, the recessed portion 337 and the tunnel portion 339 can have the same vertical width, or the tunnel portion 339 can have a greater vertical width than the recessed portion 337. In certain embodiments, the tunnel portion 339 can have a height (e.g., a clearance) of about 0.3 inch or greater.

In some embodiments, the tensioning assembly 120 is a pulley-like cabling mechanism as is well known in the art. In the illustrated embodiment, for example, the tensioning assembly 120 includes a ratcheting mechanism 122 and cables 124. The ratcheting mechanism 122 can be attached to the panel 130 in the recessed portion 337, and the cables 124 can each be (a) operably coupled to the ratcheting mechanism 122 and the strap 110 and (b) partially concealed within the tunnel portion 339 of the support panel 130. As shown, the ratcheting mechanism 122 can be fixedly attached to the support panel 130 via one or more fasteners 129 nearer to the first edge portion 136 than the second edge portion 138 of the panel 130. In some embodiments, this arrangement can inhibit or even prevent the cables 124 from contacting and potentially injuring the skin of the patient 1. In other embodiments, the tensioning assembly 120 can include more or fewer than the two illustrated cables 124 (e.g., one cable, three cables, etc.). Moreover, by mounting the tensioning assembly 120 within the channel 133, the profile (e.g., depth, height, etc.) of the device 100 can be reduced.

In some embodiments, the strap 110 can include a first forked end portion 112 ("first end portion 112") coupled to the support panel 130 within the recessed portion 337, and a second forked end portion 114 ("second end portion 114") coupled to the tensioning assembly 120. In the illustrated embodiment, for example, the first end portion 112 can be secured via fasteners (e.g., screws) 151 to the support panel 130 proximate the first edge portion 136, while each fork of the second end portion 114 can be looped through a corresponding one of the cables 124 and secured to itself via fasteners (e.g., rivets, screws, clamps, etc.) 152. Accordingly, the cables 124 can extend from the ratcheting mechanism 122, through the tunnel portion 339, and toward the second edge portion 138 of the support panel 130 to operably couple the strap 110 to the tensioning assembly 120.

When the device 100 is secured against the patient 1, the patient 1 can actuate the ratcheting mechanism 122 to selectively adjust the tension in the strap 110. In the illustrated embodiment, for example, the ratcheting mechanism 122 is a tension dial that can be rotated to retract the cables 124. Retraction of the cables 124 pulls (e.g., draws) the second end portion 114 of the strap 110 at least partially into and/or through the tunnel portion 339 of the support panel 130 and toward the first edge portion 136 of the support panel 130—thereby increasing the tension in the strap 110. In some embodiments, the ratcheting mechanism 122 can be rotated in an opposite direction or otherwise actuated to release (e.g., extend) the cables 124. This permits the second end portion 114 of the strap to move away from the first edge portion 136, at least partially through the tunnel portion 339, and/or past the second edge portion 138—thereby decreasing the tension in the strap 110. In other embodiments, the tensioning assembly 120 can have other suitable components for adjusting the tension in the strap 110 (e.g., including levers, additional pulleys, etc.). Further, in some embodiments, the support panel 130 does not include the channel 133 and the tensioning assembly 120 can be coupled to the front side of the support panel 130 such that it is not concealed within the support panel 130.

Accordingly, the device 100 allows the patient 1 to simply and easily tune (e.g., adjust) the pressure provided by the device 100 after donning the device 100. In certain embodiments, for example, the patient 1 can actuate the tensioning assembly 120 (e.g., rotate the ratcheting mechanism 122) to increase the pressure and add support to the peristomal tissues proximate the stoma to reduce the likelihood of the patient 1 developing a parastomal hernia. In particular, in certain embodiments, the device 100 can be tightened such that a mean force of about 8-40 N is applied between about 0.38 to 3.0 inches of the perimeter of the stoma of the patient 1. Moreover, in some embodiments, the device 100 enables the patient 1 to empty contents of the stoma appliance 104 without doffing the device 100. For example, the patient 1 can simply actuate the tensioning assembly 120 (e.g., rotate the ratcheting mechanism 122) on the front side of the support panel 130 to release enough pressure to empty the stoma appliance 104 without removing the device 100.

The cables 124 are not expected to become entangled with the clothing of the patient 1 or the stoma appliance 104 because the cables 124 are concealed in the tunnel portion 339 of the support panel 130—thereby improving the expected safety and durability of the device 100. The tunnel portion 339 can further inhibit or even prevent unwanted rotation of the support assembly 102 by constraining the cables 124 to generally horizontal—rather than vertical—movement. In some embodiments, for example, the device 100 does not move by more than 0.5 inch after extended wear and/or repeated movement (e.g., forward flexion, side flexion, torso torsion, etc.) by the patient 1. Similarly, the forked, angled orientation of the first and second end portions 112, 114 ("end portions 112, 114") of the strap 110 can enable the device 100 to maintain constant contact and pressure proximate the stoma of the patient 1 despite changes in abdominal wall diameter and contour. For example, the end portions 112, 114 can accommodate different angles of pull without the outer edge 134 of the support panel digging into the abdomen when the patient 1 bends in different postural positions.

In some embodiments, the strap 110 is configured to releasably secure the support assembly 102 against the patient 1 during daily use. In the illustrated embodiment, for example, the strap 110 includes a hook-and-loop fastening mechanism 115 for securing the support assembly 102 to the patient 1 without requiring significant force. In certain embodiments, no more than about 5 N of tension is required to fasten or unfasten the strap 110 using the hook-and-loop fastening mechanism 115. In some embodiments, the strap 110 and the hook-and-loop fastening mechanism 115 can have a relatively large width to make the device 100 easy to don and doff even for patients with limited dexterity (e.g., older patients). In other embodiments, the strap 110 can be secured using other suitable mechanisms (e.g., buckles, clamps, clasps, etc.). In some embodiments, the strap 110 includes a main portion 316 extending between the end portions 112, 114 and that is separable from the support assembly 102 to facilitate cleaning. In some embodiments, the strap 110 is formed from a non-elastic material such as nylon, and can include a non-slip backing that contacts the patient 1 when the device 100 is worn to further secure the device 100 around the abdomen such that it does not substantially shift position. The non-slip backing can comprise a platinum-cured silicone or similarly tacky, skin-friendly gel elastomer formed using, for example, elastomeric deposition.

In general, during use, the device 100 applies continuous pressure around the stoma to effectively flatten the abdominal wall and help keep the herniated bowel "reduced"—thereby reducing the likelihood of the patient 1 developing a parastomal hernia and/or inhibiting the worsening of an existing parastomal hernia. The device 100 is expected to increase patient comfort and patient compliance to wear the device regularly compared to conventional hernia belts because the device 100 is comparably easy to don, doff, and adjust, and because the device 100 is configured to inhibit uncomfortable shifting of the support assembly 102 during activity and postural changes. Moreover, the device 100 (e.g., the rigid support panel 130) can protect or shield the stoma from inadvertent external impacts or forces that might otherwise hurt the patient and/or potentially damage the stoma. Thus, the present technology is expected to improve outcomes and quality of life for patients living with intestinal stomas by providing safe, effective, non-invasive, and comfortable protection and abdominal wall support against parastomal herniation.

In some embodiments, one or more components of the parastomal hernia support devices described herein can be manufactured based on specific measurements of the abdomen and stoma of a patient to provide a customized and effective fit. In some embodiments, for example, the patient's abdomen can be measured using a laser scan of the abdominal wall (e.g., using a handheld laser scanner) while the patient is standing. In other embodiments, other medical imaging techniques may be used. Moreover, in some embodiments, a stoma appliance (e.g., the stoma appliance 104) can be integrated with the parastomal hernia support device to provide both support against parastomal herniation as well as stoma contents collection.

The above detailed description of embodiments of the technology are not intended to be exhaustive or to limit the technology to the precise form disclosed above. Although specific embodiments of, and examples for, the technology are described above for illustrative purposes, various equivalent modifications are possible within the scope of the technology as those skilled in the relevant art will recognize. For example, although steps are presented in a given order, alternative embodiments may perform steps in a different order. The various embodiments described herein may also be combined to provide further embodiments.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms may also include the plural or singular term, respectively.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with some embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A wearable device for applying pressure proximate to a stoma of a user wearing the device, the device comprising:
    a support panel having a front side and an opposing rear side, wherein the rear side is configured to face the user when the device is worn, and wherein the support panel is formed from a first material;
    a lining coupled to the rear side of the support panel and having an aperture therein, wherein the aperture is configured to be generally aligned with the stoma when the device is worn, and wherein the lining is formed from a second material less rigid than the first material, and
    wherein the lining has a hardness that decreases radially from the aperture; and
    a tensioning assembly coupled to the support panel and configured to selectively adjust tension in a strap securing the device to the user.

2. The device of claim 1 wherein the support panel has a generally oval shape.

3. The device of claim 1 wherein the lining includes a channel extending between the aperture and an outer edge of the lining.

4. The device of claim 3 wherein, when the device is worn by the user, the channel extends generally downward from the aperture and is configured to facilitate drainage of the stoma into a stoma appliance in fluid communication with the stoma.

5. The device of claim 1, further comprising the strap, wherein the strap is made from a non-elastic material.

6. The device of claim 1 wherein the front side of the support panel includes a recessed portion, and wherein the tensioning assembly is attached to the front side of the support panel in the recessed portion.

7. The device of claim 1 wherein:
    the support panel includes (a) an outer edge having a first edge portion and a second edge portion and (b) a channel extending along the front side between the first and second edge portions, and
    the tensioning assembly is coupled to the front side of the support panel in the channel nearer to the first edge portion than the second edge portion.

8. The device of claim 7, further comprising the strap, wherein the tensioning assembly includes:
    a ratcheting mechanism fixedly attached to front side of the support panel; and
    at least one cable coupled to the ratcheting mechanism and the strap,
    wherein actuation of the ratcheting mechanism draws the strap at least partially into the channel and toward the first edge portion.

9. A parastomal support harness, comprising:
    a generally rigid plate including an outer edge having opposing first and second edge portions;
    a cavity extending at least partially through the support plate from the second edge portion toward the first edge portion;
    a strap having a first end portion and a second end portion, wherein the first end portion is fixedly attached to the generally rigid plate proximate the first edge portion;
    a tensioning member coupled to the generally rigid plate and the second end portion of the strap, wherein the tensioning member is configured to move the second end portion of the strap at least partially through the cavity to adjust the tension in the strap; and
    a foam layer attached to a surface of the generally rigid plate and including an aperture formed therein, wherein the foam layer has a first density proximate to the outer edge and a second density proximate to the aperture that is greater than the first density.

10. The parastomal support harness of claim 9 wherein the tensioning member includes:
    a tension dial coupled to the generally rigid plate; and
    a cable extending between the tension dial and the second end portion of the strap, wherein the tension dial is rotatable to adjust the tension in the strap.

11. The parastomal support harness of claim 9 wherein the strap includes a hook-and-loop fastener between the first and second end portions.

12. The device of claim 1, further comprising the strap, wherein the strap includes:
    a first forked end portion coupled to the support panel; and
    a second forked end portion coupled to the tensioning assembly.

13. The device of claim 7 wherein the tensioning assembly is at least partially concealed within the channel.

14. The parastomal support harness of claim 9 wherein the first end portion of the strap is a first forked end portion and the second end portion of the strap is a second forked end portion.

15. The parastomal support harness of claim 9 wherein the tensioning member is at least partially concealed within the cavity.

* * * * *